(12) United States Patent
Cagle et al.

(10) Patent No.: US 6,395,746 B1
(45) Date of Patent: May 28, 2002

(54) METHODS OF TREATING OPHTHALMIC, OTIC AND NASAL INFECTIONS AND ATTENDANT INFLAMMATION

(75) Inventors: Gerald Cagle; Robert L. Abshire, both of Fort Worth; David W. Stroman, Irving; John M. Yanni, Burleson, all of TX (US)

(73) Assignee: Alcon Manufacturing, Ltd., Fort Worth, TX (US)

(*) Notice: Subject to any disclaimer, the term of this patent is extended or adjusted under 35 U.S.C. 154(b) by 0 days.

(21) Appl. No.: 09/646,799

(22) PCT Filed: Sep. 9, 1999

(86) PCT No.: PCT/US99/22624

§ 371 (c)(1),
(2), (4) Date: Sep. 22, 2000

(87) PCT Pub. No.: WO00/18388

PCT Pub. Date: Apr. 6, 2000

Related U.S. Application Data

(60) Provisional application No. 60/102,508, filed on Sep. 30, 1998, and provisional application No. 60/102,509, filed on Sep. 30, 1998.

(51) Int. Cl.[7] .................. A61K 31/44; A61K 31/58; A61K 31/56; A61K 31/40; A61K 31/65
(52) U.S. Cl. .............. 514/300; 514/174; 514/179; 514/180; 514/181; 514/413; 514/619
(58) Field of Search .................. 514/300, 174, 514/179, 180, 181, 413, 619

(56) References Cited

U.S. PATENT DOCUMENTS

| | | | |
|---|---|---|---|
| 4,474,751 A | 10/1984 | Haslam et al. | |
| 4,551,456 A | 11/1985 | Katz | |
| 4,670,444 A | 6/1987 | Grohe et al. | |
| 4,710,495 A | 12/1987 | Bodor | |
| 4,730,013 A | 3/1988 | Bondi et al. | |

(List continued on next page.)

FOREIGN PATENT DOCUMENTS

| | | |
|---|---|---|
| CA | 2086914 | 7/1993 |
| EP | 0 982 031 | 3/2000 |
| ES | S/N 08320 | 4/1993 |
| WO | WO 90/01933 | 3/1990 |
| WO | WO 96/39146 | 12/1996 |

(List continued on next page.)

OTHER PUBLICATIONS

Blondeau, Joseph M., A review of the comparative in-vitro activities of 12 antimicrobial agents, with focus on five new 'respiratory quinolones', *Journal of Antimicrobial Chemotherapy*, vol. 43, Suppl. B, pp. 1–11 (1999).

Elies, W., "Novel fluoroquinolones in the treatment of ENT infections", *Chemotherapie Journal*, 7/3, pp. 93–97 (1998) (no translation); XP000892813.

Ernst et al., "Levofloxacin and trovafloxacin: The next generation of fluoroquinolones?", Clinical Review, *Am. J. Health–Syst. Pharm.*, vol. 54, pp. 2569–2584 (114/15/97).

Gootz et al., "Fluoroquinolone antibacterials: SAR mechanism of action, resistance, and clinical aspects", *Medicinal Research Reviews*, vol. 16, pp. 433–486 (1996).

Kaw et al., "The penetration of trovafloxacin into the eye and CSF of rabbits", IOVS, vol. 40, No. 4, p. S88 (Mar. 15, 1999); XP–000892619.

Kraseman et al., "Efficacy of Moxifloxacin against Staphylococcus aureus in respiratory tract and skin and skin structure infections", *Jornal of Antimicrobial Chemotherapy*, vol. 44, No. Suppl. A, pp. 150 (Jul. 1999); XP000892776.

McLeod et al., "The effect of topical trovafloxacin in a rabbit streptococcus pneumoniae keratitis model", IOVS vol. 40, No. 4, p. S689 (Mar. 15, 1999) XP–000892625.

NCCLS Document M7–A4, "Methods for Dilution Antimicrobial Susceptability Tests for Bacteria That Grow Aerobically", 4th Edition, 1997.

"New Antimicrobial Agents Approved by the U.S. Food and Drug Administration in 1997 and New Indications for Previously Approved Agents" *Antimicrobial Agents and Chemotherapy*, vol. 42, No. 4, pp. 987–988 (Apr. 1, 1998); XP000872060.

NG et al., "Treatment of experimental staphylococcus epidermidis endophthalmitis with oral trovafloxacin" *American Journal of Ophthalmology*, vol. 216 (2), pp. 278–287 (Aug. 1998).

Patent Abstracts of Japan, vol. 1998, No. 10 (Aug. 31, 1998), JP 10 130148 May 19, 1998 abstract.

Patent Abstracts of Japan, vol. 012, No. 472 (Dec. 9, 1988), JP 63 190826 Aug. 8, 1988 abstract.

Pediatric Research, 104th Annual Meeting of the American Pediatric Society and the 63rd Annual meeting of the Society for Pediatric Research, vol. 35, No. 4, Part 2, p. 191A, Seattle, Washington (05/02–05/94).

Tillotson, G, S., "Quinolones: structure–activity relationships and future predictions", *J. of Medical Microbiology*, vol. 44, pp. 320–324 (1996).

Vincent et al., "Pharmacokinetics and safety of trovalfloxacin in healthy male volunteers following administration of single intravenous doses of the prodrug, alatrofloxacin", *Journal of Antimicrobial Chemotherapy*, vol. 39, Suppl. B, pp. 75–80. (Jan. 1, 1997).

(List continued on next page.)

*Primary Examiner*—William R. A. Jarvis
(74) *Attorney, Agent, or Firm*—Gregg C. Brown

(57) ABSTRACT

Methods of treating or preventing ophthalmic, otic, and nasal infections and attendant inflammation are described. The methods utilize ophthalmic, otic, and nasal compositions containing a new class of antibiotics (e.g. trovafloxacin). The compositions also contain one or more anti-inflammatory agents (e.g. dexamethasone). The compositions are utilized to treat ophthalmic, otic, and nasal conditions by topically applying the compositions to the affected tissues.

11 Claims, No Drawings

U.S. PATENT DOCUMENTS

| | | |
|---|---|---|
| 4,844,902 A | 7/1989 | Grohe |
| 4,920,120 A | 4/1990 | Domagala et al. |
| 4,980,470 A | 12/1990 | Masuzawa et al. |
| 4,990,517 A | 2/1991 | Petersen et al. |
| 4,996,335 A | 2/1991 | Bodor |
| 5,059,597 A | 10/1991 | Petersen et al. |
| 5,149,694 A | 9/1992 | Cagle et al. |
| 5,164,402 A | 11/1992 | Brighty |
| 5,185,337 A | 2/1993 | Fujii et al. |
| 5,223,493 A | 6/1993 | Boltralik |
| 5,416,096 A | 5/1995 | Petersen et al. |
| 5,480,879 A | 1/1996 | Petersen et al. |
| 5,540,930 A | 7/1996 | Guy et al. |
| 5,563,138 A | 10/1996 | Ueda et al. |
| 5,597,560 A | 1/1997 | Bergamini et al. |
| 5,609,942 A | 3/1997 | Petersen et al. |
| 5,631,004 A | 5/1997 | Cagle et al. |
| 5,665,373 A | 9/1997 | Robertson et al. |
| 5,679,665 A | 10/1997 | Bergamini et al. |
| 5,849,752 A | 12/1998 | Grunenberg et al. |
| 5,854,241 A | 12/1998 | Hallenbach et al. |
| 5,912,255 A | 6/1999 | Bussell |

FOREIGN PATENT DOCUMENTS

| | | |
|---|---|---|
| WO | WO 98/06435 | 2/1998 |
| WO | WO 99/15172 | 4/1999 |
| WO | WO 00/18386 | 4/2000 |
| WO | WO 00/18387 | 4/2000 |
| WO | WO 00/18388 | 4/2000 |
| WO | WO 00/18404 | 4/2000 |

OTHER PUBLICATIONS

Weiss, Lee R., "Therapeutic Pathways for Antimicrobial Use: General Overview", *The American Journal Of Managed Care*, vol. 4, No. 10, Sup., pp. S543–S549 (1988).

Wentland, Mark P., "Structure–activity relationships of fluoroquinolones", *The New Generation of Quinolones*, (Siporin, C., Heifetz, C. L. & Domagala, J. M., Eds), pp. 1–43, Marcel Dekker, New York (1990).

Senturia, Ben, "Etiology Of External Otitis", *Larynyoscope*, vol. 55, pp. 277–293 (1945).

METHODS OF TREATING OPHTHALMIC, OTIC AND NASAL INFECTIONS AND ATTENDANT INFLAMMATION

This application is 371 of PCT/US99/22624, filed Sep. 29, 1999, which claims priority to provisional application Nos. 60/102,508 and 60/102,509, both filed Sep. 30, 1998.

BACKGROUND OF THE INVENTION

The present invention is directed to the provision of topical antibiotic pharmaceutical compositions for the treatment of ophthalmic, otic and nasal infections, particularly bacterial infections, and to methods of treating ophthalmic, otic and nasal infections by applying those compositions to the affected tissues. The compositions and methods of the invention are based on the use of a new class of antibiotics. The compositions of the present invention may also contain one or more anti-inflammatory agents.

The use of quinolone antibiotics to treat infections represents the current state of the art in the field of ophthalmic pharmaceutical compositions and methods of treatment. For example, a topical ophthalmic composition containing the quinolone ciprofloxacin is marketed by Alcon Laboratories, Inc. under the name CILOXAN™ (Ciprofloxacin 0.3%) Ophthalmic Solution. The following quinolones have also been utilized in ophthalmic antibiotic compositions:

| Quinolone | Product | Manufacturer |
|---|---|---|
| Ofloxacin | OCUFLOX ™ | Allergan |
| Norfloxacin | CHIBROXIN ™ | Merck |
| Lomefloxacin | LOMEFLOX ™ | Senju |

The foregoing quinolone antibiotic compositions are generally effective in treating ophthalmic infections, and have distinct advantages over prior ophthalmic antibiotic compositions, particularly those having relatively limited spectrums of antimicrobial activity, such as: neomycin, polymyxin B, gentamicin and tobramycin, which are primarily useful against gram negative pathogens; and bacitracin, gramicidin, and erythromycin, which are primarily active against gram positive pathogens. However, despite the general efficacy of the ophthalmic quinolone therapies currently available, there is a need for improved compositions and methods of treatment based on the use of antibiotics that are more effective than existing antibiotics against key ophthalmic pathogens, and less prone to the development of resistance by those pathogens.

There is an even greater need for effective topical compositions and methods for treating otic and nasal infections, particularly bacterial infections. The use of oral antibiotics to treat otic infections in children has limited efficacy, and creates a serious risk of pathogen resistance to the orally administered antibiotics.

Ophthalmic, otic and nasal infections are frequently accompanied by inflammation of the infected ophthalmic, otic and nasal tissues and perhaps even surrounding tissues. Similarly, ophthalmic, otic and nasal surgical procedures that create a risk of microbial infections frequently also cause inflammation of the affected tissues. Thus, there is also a need for ophthalmic, otic and nasal pharmaceutical compositions that combine the anti-infective activity of one or more antibiotics with the anti-inflammatory activity of one or more steroid or non-steroid agents in a single composition.

SUMMARY OF THE INVENTION

The invention is based on the use of a potent new class of antibiotics to treat ophthalmic, otic and nasal infections, as well as the prophylactic use of these antibiotics following surgery or other trauma to ophthalmic, otic or nasal tissues. The compositions of the present invention may also be administered to the affected tissues during ophthalmic, otic or nasal surgical procedures to prevent or alleviate post-surgical infections.

The compositions preferably also contain one or more anti-inflammatory agents to treat inflammation associated with infections of ophthalmic, otic or nasal tissues. The anti-inflammatory component of the compositions is also useful in treating inflammation associated with physical trauma to ophthalmic, otic or nasal tissues, including inflammation resulting from surgical procedures. The compositions of the present invention are therefore particularly useful in treating inflammation associated with trauma to ophthalmic, otic or nasal tissues wherein there is either an infection or a risk of an infection resulting from the trauma.

Examples of ophthalmic conditions that may be treated with the compositions of the present invention include conjunctivitis, keratitis, blepharitis, dacryocystitis, hordeolum and corneal ulcers. The compositions of the invention may also be used prophylactically in connection with various ophthalmic surgical procedures that create a risk of infection.

Examples of otic conditions that may be treated with the compositions of the present invention include otitis externa and otitis media. With respect to the treatment of otitis media, the compositions of the present invention are primarily useful in cases where the tympanic membrane has ruptured or tympanostomy tubes have been implanted. The compositions may also be used to treat infections associated with otic surgical procedures, such as tympanostomy, or to prevent such infections.

The compositions of the present invention are specially formulated for topical application to ophthalmic, otic and nasal tissues. The compositions are preferably sterile, and have physical properties (e.g., osmolality and pH) that are specially suited for application to ophthalmic, otic and nasal tissues, including tissues that have been compromised as the result of preexisting disease, trauma, surgery or other physical conditions.

DETAILED DESCRIPTION OF THE INVENTION

The antibiotics used in the compositions and methods of the present invention have the following formula:

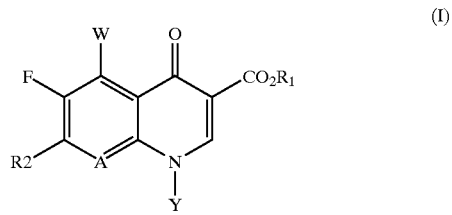

(I)

wherein
R1 is hydrogen, a pharmaceutically acceptable cation, or (C1–C6) alkyl;
Y, when taken independently, is ethyl, t-butyl, vinyl, cyclopropyl, 2-fluoroethyl, p-fluorophenyl, or o,p-difluorophenyl;

W is hydrogen, F, C1, Br, C1–C4 alkyl, C1–C4 alkoxy, NH2 or NHCH3;

A is CH, CF, CC1, COCH3, C—CH3, C—CN or N; or

A is carbon and is taken together with Y and the carbon and nitrogen to which A and Y are attached to form a five or six membered ring which may contain oxygen or a double bond, and which may have attached thereto R8 which is methyl or methylene; and R2 is

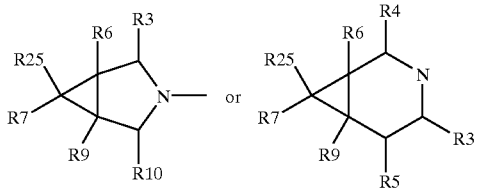

wherein:

R3, R4, R5, R6, R7, R9, R10 and R25 are each independently H, CH3, CH2NH2, CH2NHCH3 or CH2NHC2H5, and R5, R6, R7 and R9 may also independently be NH2, NHCH3 or NHC2H5, provided that not more than three of R3, R4, R5, R6, R7, R9, R10 and R25 are other than hydrogen, and if three of these substituents are not hydrogen, at least one of them is methyl.

The antibiotics utilized in the present invention also include prodrugs of the compounds of formula (I) having a free amino group, as well as pharmaceutically useful hydrates and salts of the compounds of formula (I).

The compound Trovafloxacin is most preferred. Trovafloxacin has the following structure:

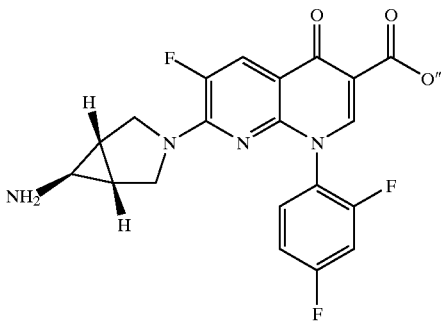

Further details regarding the structure, preparation, and physical properties of Trovafloxacin and other compounds of formula (I) are provided in U.S. Pat. No. 5,164,402.

The concentrations of the antibiotics of formula (I) in the compositions of the present invention will vary depending on the intended use of the compositions (e.g., treatment of existing infections or prevention of post-surgical infections), and the relative antimicrobial activity of the specific antibiotic selected. The antimicrobial activity of antibiotics is generally expressed as the minimum concentration required to inhibit the growth of a specified pathogen. This concentration is also referred to as the "minimum inhibitory concentration" or "MIC". The term "MIC90" refers to the minimum concentration of antibiotic required to inhibit the growth of ninety percent (90%) of the strains of a species. The concentration of an antibiotic required to totally kill a specified bacteria is referred to as the "minimum bactericidal concentration" or "MBC". The minimum inhibitory concentration of Trovafloxacin for several bacteria commonly associated with ophthalmic, otic and nasal infections are provided in the following table:

| Microorganism | $MIC_{90}$ |
| --- | --- |
| S. aureus/methicillin sensitive | 0.03 |
| S. aureus/methicillin resistant | 2.0 |
| S. aureus/quinolone resistant | 4.0 |
| S. epidermidis/methicillin sensitive | 0.06 |
| S. epidermidis/methicillin resistant | 4.0 |
| S. pneumoniae/penicillin sensitive | 0.25 |
| S. pneumoniae/penicillin resistant | 0.25 |
| P. aeruginosa | 2.0 |
| H. influenzae/β-lactamase positive | 0.03 |
| H. influenzae/βlactamase negative | 0.03 |

All of the foregoing concentrations are expressed as micrograms per milliliter ("mcg/ml").

The appropriate antibiotic concentration for ophthalmic compositions will generally be an amount of one or more antibiotics of formula (I) sufficient to provide a concentration in the aqueous humor and lacrimal fluid of the eye equal to or greater than the MIC90 level for the selected antibiotic (s) relative to gram-negative and gram-positive organisms commonly associated with ophthalmic infections. The appropriate concentration for otic and nasal compositions will generally be an amount of one or more antibiotics of formula (I) sufficient to provide a concentration in the infected tissues equal to or greater than the MIC90 level for the selected antibiotic(s), relative to gram-negative and gram-positive organisms commonly associated with otic or nasal infections. Such amounts are referred to herein as "an antimicrobial effective amount". The compositions of the present invention will typically contain one or more compounds of formula (I) in a concentration of from about 0.1 to about 1.0 percent by weight ("wt. %") of the compositions.

The compositions of the present invention may also contain one or more anti-inflammatory agents. The anti-inflammatory agents utilized in the present invention are broadly classified as steroidal or non-steroidal. The preferred steroidal anti-inflammatory agents are glucocorticoids.

The preferred glucocorticoids for ophthalmic and otic use include dexamethasone, loteprednol, rimexolone, prednisolone, fluorometholone, and hydrocortisone. The preferred glucocorticoids for nasal use include mometasone, fluticasone, beclomethasone, flunisolide, triamcinolone and budesonide.

The dexamethasone derivatives described in U.S. Pat. No. 5,223,493 (Boltralik) are also preferred steroidal anti-inflammatory agents, particularly with respect to compositions for treating ophthalmic inflammation. The following compounds are especially preferred:

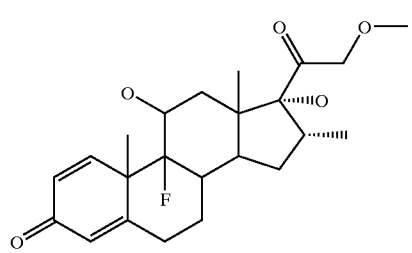

AL-1529

AL-2512

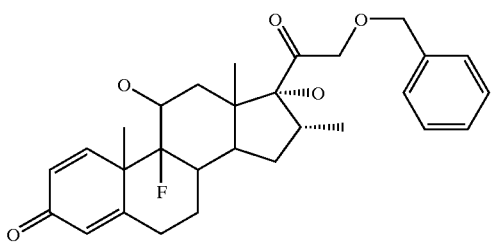

These compounds are referred to herein as "21 -ether derivatives of dexamethasone". The 21-benzyl ether derivative (i.e.. compound AL-2512) is particularly preferred.

The preferred non-steroidal anti-inflammatory agents are: prostaglandin H synthetase inhibitors (Cox I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, NCX-4016, HCT-1026, NCX-284, NCX-456, tenoxicam and carprofen; cyclooxygenase type II selective inhibitors, such as NS-398, vioxx, celecoxib, P54, etodolac, L-804600 and S-33516; PAF antagonists, such as SR-27417, A-137491, ABT-299, apafant, bepafant, minopafant, E-6123, BN-50727, nupafant and modipafant; PDE IV inhibitors, such as ariflo, torbafylline, rolipram, filaminast, piclamilast, cipamfylline, CG-1088, V-11294A. CT-2820, PD-168787, CP-293121 DWP-205297, CP-220629, SH-636, BAY-19-8004, and roflumilast; inhibitors of cytokine production, such as inhibitors of the NFkB transcription factor; or other anti-inflammatory agents known to those skilled in the art.

The concentrations of the anti-inflammatory agents contained in the compositions of the present invention will vary based on the agent or agents selected and the type of inflammation being treated. The concentrations will be sufficient to reduce inflammation in the targeted ophthalmic, otic or nasal tissues following topical application of the compositions to those tissues. Such an amount is referred to herein as "an anti-inflammatory effective amount". The compositions of the present invention will typically contain one or more anti-inflammatory agents in an amount of from about 0.01 to about 1.0 wt.%.

The compositions are typically administered to the affected ophthalmic, otic or nasal tissues by topically applying one to four drops of a sterile solution or suspension, or a comparable amount of an ointment, gel or other solid or semisolid composition, one to four times per day. However, the compositions may also be formulated as irrigating solutions that are applied to the affected ophthalmic, otic or nasal tissues during surgical procedures.

The ophthalmic, otic, and nasal compositions of the present invention will contain one or more compounds of formula (I) and preferably one or more anti-inflammatory agents, in pharmaceutically acceptable vehicles. The compositions will typically have a pH in the range of 4.5 to 8.0. The ophthalmic compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

Ophthalmic, otic, and nasal products are typically packaged in multidose form. Preservatives are thus required to prevent microbial contamination during use. Suitable preservatives include: polyquaternium-1, benzalkonium chloride, thimerosal, chlorobutanol, methyl paraben, propyl paraben, phenylethyl alcohol, edetate disodium, sorbic acid, or other agents known to those skilled in the art. The use of polyquaternium-1 as the antimicrobial preservative is preferred. Typically such preservatives are employed at a level of from 0.001% to 1.0% by weight.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g.. Pluronic F-68, F-84 and P-103), cyclodextrin, or other agents knoat to those skilled in the art. Typically such co-solvents are employed at a level of from 0.01% to 2% by weight.

The use of viscosity enhancing agents to provide the compositions of the invention with viscosities greater than the viscosity of simple aqueous solutions may be desirable to increase absorption of the active compounds by the target tissues or increase the retention time in the eye, ear or nose. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

The following examples are provided to further illustrate the ophthalmic, otic, and nasal compositions of the present invention.

EXAMPLE 1

Ophthalmic/Otic/Nasal Solution

| Ingredient | Amount (wt. %) |
|---|---|
| Trovafloxacin | 0.35 |
| Sodium Acetate | 0.03 |
| Acetic Acid | 0.04 |
| Mannitol | 4.60 |
| EDTA | 0.05 |
| Benzalkonium Chloride | 0.006 |
| Water | q.s. 100 |

EXAMPLE 2

Ophthalmic/Otic/Nasal Suspension

| Ingredient | Amount (wt. %) |
|---|---|
| Trovafloxacin | 0.3 |
| Dexamethasone, Micronized USP | 0.10 |
| Benzalkonium Chloride | 0.01 |
| Edetate Disodium, USP | 0.01 |
| Sodium Chloride, USP | 0.3 |
| Sodium Sulfate, USP | 1.2 |
| Tyloxapol, USP | 0.05 |
| Hydroxyethylcellulose | 0.25 |
| Sulfuric Acid and/or Sodium Hydroxide, NF | q.s. for pH adjustment to 5.5 |
| Purified Water, USP | q.s. to 100 |

EXAMPLE 3

| Ophthalmic Ointment | |
|---|---|
| Ingredient | Amount (wt. %) |
| Trovafloxacin | 0.35 |
| Mineral Oil, USP | 2.0 |
| White petrolatium, USP | q.s 100 |

EXAMPLE 4

| Ophthalmic Ointment | |
|---|---|
| Ingredient | Amount (wt. %) |
| Trovafloxacin | 0.3 |
| Fluorometholone Acetate, USP | 0.1 |
| Chlorobutanol, Anhydrous, NF | 0.5 |
| Mineral Oil, USP | 5 |
| White Petrolatum, USP | q.s. 100 |

The invention has been described herein by reference to certain preferred embodiments. However, as obvious variations thereon will become apparent to those skilled in the art, the invention is not to be considered as limited thereto.

What is claimed is:

1. A method of treating or preventing ophthalmic, otic or nasal infections and attendant inflammation, which comprises topically applying a therapeutically effective amount of a topical ophthalmic, otic or nasal pharmaceutical composition to the affected tissues, said composition comprising one or more compounds of the formula:

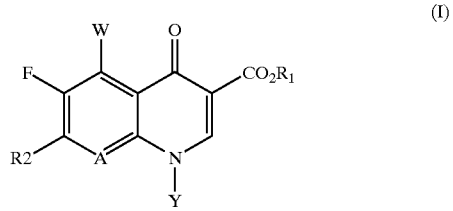

(I)

wherein

R1 is hydrogen, a pharmaceutically acceptable cation, or (C1–C6) alkyl;

Y, when taken independently, is ethyl, t-butyl, vinyl, cyclopropyl, 2-fluoroethyl, p-fluorophenyl, or o,p-difluorophenyl;

W is hydrogen, F, Cl, Br, C1–C4 alkyl, C1–C4 alkoxy, $NH_2$ or $NHCH_3$;

A is CH, CF, CCl, $COCH_3$, C—$CH_3$, C—CN or N; or

A is carbon and is taken together with Y and the carbon and nitrogen to which A and Y are attached to form a five or six membered ring which may contain oxygen or a double bond, and which may have attached thereto R8 which is methyl or methylene; and R2 is

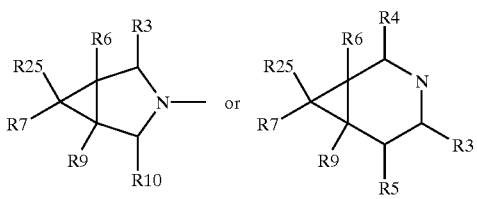

wherein:

R3, R4, R5, R6, R7, R9, R10 and R25 are each independently H, $CH_3$, $CH_2NH_2$, $CH_2NHCH_3$ or $CH_2NHC_2H_5$, and R5, R6, R7, and R9 may also independently be $NH_2$, $NHCH_3$ or $NHC_2H_5$, provided that not more than three of R3, R4, R5, R6, R7, R9, R10 and R25 are other than hydrogen, and if three of these substituents are not hydrogen, at least one of them is methyl; or a prodrug of a compound of formula (I) having a free amino group, or a pharmaceutically useful hydrate or salt of a compound of formula (I);

an anti-inflammatory effective amount of a steroidal or non-steroidal anti-inflammatory agent; and a pharmaceutically acceptable vehicle therefor.

2. A method according to claim 1, wherein the ant-inflammatory agent comprises a glucocorticoid.

3. A topical composition according to claim 2, wherein the glucocorticoid is selected from the group consisting of dexamethasone, AL1529, AL2512, rimexolone, prednisolone, fluorometholone, hydrocortisone, mometasone, fluticasone, beclomethasone, flunisolide, triamcinolone and budesonide.

4. A topical composition according to claim 1, wherein the anti-inflammatory agent comprises a non-steroidal agent selected from the group consisting of prostaglandin H synthetase inhibitors, PAF antagonists, and PDE IV inhibitors.

5. A method according to claim 1, wherein the compound of formula (I) comprises trovafloxacin.

6. A method according to any one of claim 2, 3, or 4, or wherein the compound of formula (I) comprises trovafloxacin.

7. A method according to any one of claim 1, 2, 3, 4, or 5, or wherein the composition is topically applied to the eye to treat ophthalmic infections and attendant inflammation.

8. A method according to any one of claim 1, 2, 3, 4, or 5, wherein the composition is topically instilled in the ear to treat otic infections and attendant inflammation.

9. A method of claim 1 or claim 5, wherein the anti-inflammatory agent comprises dexamethasone.

10. A method according to claim 1 or claim 5, wherein the anti-inflammatory agent comprises nepafenac.

11. A method according to claim 1 or claim 5, wherein the anti-inflammatory agent comprises ketoralac.

* * * * *

UNITED STATES PATENT AND TRADEMARK OFFICE
CERTIFICATE OF CORRECTION

PATENT NO. : 6,395,746 B1
DATED : May 28, 2002
INVENTOR(S) : Gerald Cagle et al.

It is certified that error appears in the above-identified patent and that said Letters Patent is hereby corrected as shown below:

<u>Title page,</u>
Item [22], should read -- PCT Filed: Sep. 29, 1999 --

Signed and Sealed this

Fifteenth Day of April, 2003

JAMES E. ROGAN
*Director of the United States Patent and Trademark Office*